United States Patent [19]

McKinney

[11] Patent Number: 4,901,416
[45] Date of Patent: Feb. 20, 1990

[54] CONTROL SYSTEM FOR MANUFACTURING ENHANCED TUBES

[75] Inventor: Craig J. McKinney, Fulton, N.Y.
[73] Assignee: Carrier Corporation, Syracuse, N.Y.
[21] Appl. No.: 809,465
[22] Filed: Dec. 16, 1985
[51] Int. Cl.$^4$ .............................................. B21D 53/02
[52] U.S. Cl. ....................................... 29/726; 29/407; 29/890.035; 29/890.045; 29/890.07
[58] Field of Search .................. 29/157.4, 407, 703, 29/705, 714, 726, 709, 157.3 R, 720; 73/168, 38, 37.5

[56] References Cited

U.S. PATENT DOCUMENTS

| | | | |
|---|---|---|---|
| 2,390,252 | 12/1945 | Hayward | 73/37.5 |
| 3,577,642 | 5/1971 | Tripoli | 73/37.5 |
| 4,001,359 | 1/1977 | Fisher et al. | 73/37.5 |
| 4,098,408 | 7/1978 | Miller, Jr. et al. | 73/37.5 |
| 4,103,535 | 8/1978 | Mutter et al. | 73/37.5 |

Primary Examiner—Howard N. Goldberg
Assistant Examiner—Irene Cuda
Attorney, Agent, or Firm—Robert H. Kelly

[57] ABSTRACT

A method and control system for manufacturing externally enhanced evaporator tubes. A pressure signal indicative of the pore size on the external surface of the enhanced evaporator tube is provided to a microcomputer system which processes the signal indicative of the pore size and compares the signal to a predetermined pore size signal to determine when the pore size is within a selected tolerance. The microcomputer generates a control signal to adjust the enhancing process if the microcomputer system determines that the pore size of the manufactured tube is different than the selected pore size.

2 Claims, 4 Drawing Sheets

CONTROL SYSTEM FOR MANUFACTURING ENHANCED TUBES

BACKGROUND OF THE INVENTION

This invention relates generally to enhanced evaporator tubes, and more particularly, to a method and closed loop control system for manufacturing externally enhanced tubes.

In an evaporatory of certain refrigeration systems a fluid to be cooled is passed through heat transfer tubing while refrigerant in contact with the exterior of the tubing changes state from a liquid to a vapor by absorbing heat from the fluid within the tubing. The external and internal configuration of the tubing are important in determining the overall heat transfer characteristics of the tubing. For example, it is known that one of the most effective ways of transferring heat from the fluid within the tube to the boiling refrigerant surrounding the tube is through the mechanism of nucleate boiling.

It has been theorized that the provision of vapor entrapment sites or cavities on a heat transfer surface cause nucleate boiling. According to this theory the vapor trapped in the cavities forms the nucleus of a bubble at or slightly above the saturation temperature, and the bubble increases in volume as heat is added until surface tension is overcome and the vapor bubble breaks free from the heat transfer surface. As the vapor bubble leaves the heat transfer surface, liquid enters the vacated volume trapping the remaining vapor and another bubble is formed. The continual bubble formation together with the convection effect of the bubbles traveling through and mixing the boundary layer of superheated refrigerant, which covers the vapor entrapment sites, results in improved heat transfer. A heat exchange surface having a number of discrete artificial nucleation sites is disclosed in U.S. Pat. No. 3,301,314.

It is known that a vapor entrapment site or cavity produces stable bubble columns when it is of the re-entrant type. In this context, a re-entrant vapor entrapment site is defined as a cavity or groove in which the size of the surface pore or gap is smaller than the subsurface cavity or subsurface groove. Heat transfer tubes having re-entrant type grooves are disclosed in U.S. Pat. Nos. 3,696,861 and 3,768,290.

It has been discovered that an excessive influx of liquid from the surroundings can flood or de-activate a re-entrant type vapor entrapment site. However, a heat transfer surface having subsurface channels communicating with the surroundings through surface openings or pore having a specified "opening ratio" have been found to provide good heat transfer and prevent flooding of the vapor entrapment site or subsurface channel.

In regard to the interior surface configuration of a heat transfer tube, it is known that providing an internal rib on the tube may enhance the heat transfer characteristics of the tube due to the increased turbulence of the fluid flowing through the ribbed tube.

As disclosed in U.S. Pat. Nos. 4,425,696 and 4,438,807 assigned to the present assignee and incorporated by reference herein, an internally and externally enhanced heat transfer tube, having an internal rib and an external helical fin (creating a subsurface channel) communicating with the surrounding liquid through surface openings (pores) is manufactured by a single pass process with a tube finning and rolling machine. According to the disclosed process a grooved mandrel is placed inside an unformed tube and a tool arbor having a tool gang thereon is rolled over the external surface of the tube. The unformed tube is pressed against the mandrel to form at least one internal rib on the internal surface of the tube. Simultaneously, at last one external fin convolution is formed on the external surface of the tube by finning discs on the tool gang. The external fin convolutions form subsurface channels therebetween. The external fin convolutions also have depressed sections above the internal rib where the tube is forced into the grooves of the mandrel to form the rib. A smooth roller-like disk on the tool arbor is rolled over the external surface of the tube after the external fin convolution is formed. The smooth roller-like disc is designed to bend over the tip portion of the external fin so that it touches the adjacent fin convolution and forms an enclosed subsurface channel. However, the tip portion of the depressed sections of the external fin, which are located above the internal rib, are also bent over but do not touch the adjacent convolutions, thereby forming pores which provide fluid communication between the fluid surrounding the tube and the subsurface channels.

The performance of the foregoing tube is critically dependent upon the external enhancement of the tube. It is therefore important to maintain a consistent subsurface channel size and pore size during the manufacturing process. Normal variations in subsurface channel size and surface pore size do occur, however, due to tool wear, material variations in the tube, dimensional variations in the tube lengths, and machine tolerances. In order to account for these variables and maintain a consistent pore size, it is necessary to measure the pore size on each tube produced and adjust the finning machine to maintain the correct subsurface and pore sizes. However, the prior methods of checking the pore size in an enhanced tube and adjusting the finning machine were very laborious and expensive processes, and were very difficult to use in a manufacturing process. For example, one method was to have an operator randomly select a manufactured tube and optically check the pore size of the selected tube under a microscope. Another method was to take a photograph of a tube and using an image analyzer compare the area of the pores in a selected area to the area of the pores in a reference photograph. After determining the size of the pores, the operator would then adjust the finning machine to compensate for any variations in the desired pore size. However, these methods were time consuming and did not provide the quality and quantity of tubes necessary for a manufacturing process.

Thus, there is a clear need for a method and control system for manufacturing enhanced tubes that would, to a large extent, overcome the inadequacies that have characterized the prior art.

SUMMARY OF THE INVENTION

A closed loop electronic control system for manufacturing enhanced tubes has been developed. This control system is characterized by at least one pressure transducer which measures the average pore size on the enhanced tube surface and transmits an output signal corresponding to the size of the pores to a microcomputer which analyzes the pressure transducer signals and sends an output signal to a programmable controller, which in turn controls a servo motor for adjusting the finning machine to maintain the correct cavity size.

Accordingly, it is an object of the present invention to provide a method and control system which measures the average pore size of an enhanced tube surface and automatically adjusts the finning machine to maintain the correct cavity size.

Another object of the present invention is to provide a method and control system which can inspect 100% of the enhanced tubes and adjust the finning machine to maintain the correct cavity size on every tube produced.

A further object of the present invention is to provide a method and control system which would reduce down time of the finning machines due to mechanical adjustments of the finning heads.

These and other objects of the present invention are obtained by a novel method and control system for measuring the pore size on an enhanced evaporator tube and automatically adjusting the finning machine to maintain the correct pore size. The control system comprises at least one pressure transducer that provides an electrical analog signal to a signal conditioner which amplifies and linearizes the signal and feeds it to a microcomputer. The microcomputer compares the input signals to a reference signal and generates an output signal to a programmable controller which generates a digital signal to be fed to a motion controller. The output signal of the motion controller is fed to a servo motor which in turn moves a linear actuator to adjust the finning head. Thus, the present invention measures the average pore size of an enhanced tube and adjusts the finning machine to maintain the correct pore size.

The various features of novelty which characterize the invention are pointed with particularity in the claims annexed to and forming a part of this specification. For a better understanding of the invention, its operating advantages and specific objects attained by its use, reference should be had to the accompanying drawings and descriptive matter in which there is illustrated and described a preferred embodiment of the invention.

BRIEF DESCRIPTION OF THE DRAWINGS

Other objects and advantages of the present invention will be apparent from the following detailed description in conjunction with the accompanying drawings, forming a part of this specification, and in which reference numerals shown in the drawing designate like or corresponding parts throughout the same, in which.

DESCRIPTION OF THE PREFERRED EMBODIMENT

The embodiment of the present invention described below is specially designed for use with enhanced evaporator tubes because these tubes have a critical dimension which must be precisely controlled in order to maintain good heat transfer performance. These enhanced tubes are designed for use in an evaporator of a refrigeration system having a fluid to be cooled passing through the tubes and having refrigerant, which is to be vaporized, in contact with the external surfaces of the tubes. Typically, a plurality of heat transfer tubes are mounted in parallel and connected so that several tubes form a fluid flow circuit and a plurality of such parallel circuits are provided to form a tube bundle. Usually, all of the tubes of the various circuits are contained within a single shell wherein they are immersed in the refrigerant. The heat transfer capability of the evaporator is largely determined by the average heat transfer characteristics of the heat transfer tubes. Thus, the size of the subsurface channels and pores on the surface of the tube are critical. Therefore, it is important to maintain a consistent subsurface channel size and pore size during the manufacturing process of the enhanced evaporator tube.

Figure 1:
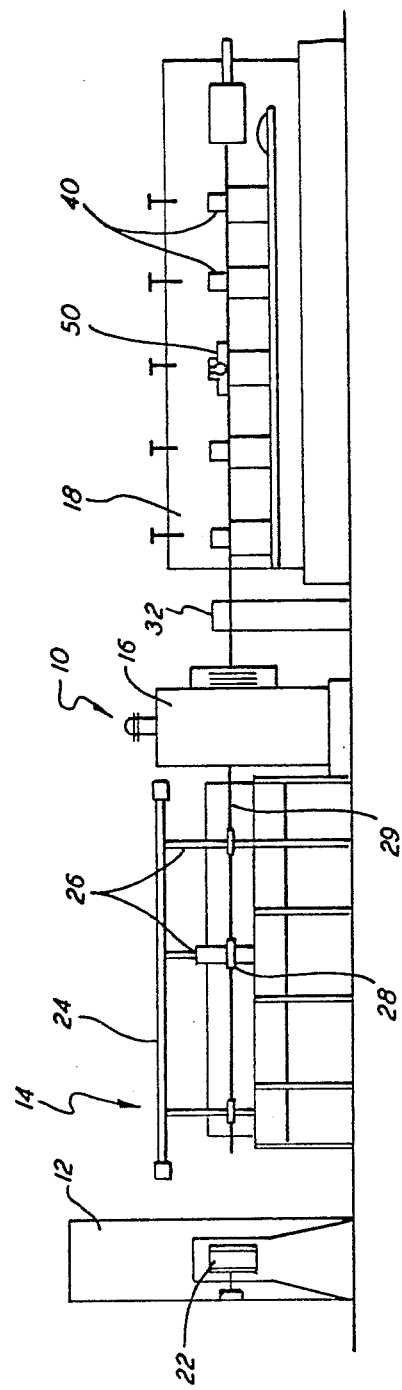
FIG. 1 is a schematic representation of a finning machine for the manufacture of enhanced tubes in accordance with the present invention.

Referring now to the drawings, FIG. 1 is a diagrammatic representation of a finning station for manufacturing enhanced tubes in accordance with the principles of the present invention. The finning station 10 includes an electronic control cabinet 12, a feed station 14, a finning head section 16, an ejection section 32, and a pore measurement section 18. The electronic control cabinet includes a microcomputer, a programmable controller, and an operator console 22. The microcomputer determines whether the process is within control tolerances and the programmable controller performs logic execution, timing, sequencing, and calculations for the finning operation. The feed section 14 generally includes two similar parallel mandrels 24 (the two mandrels are generally in the same horizontal plane, thus, the rearward mandrel is not shown in the Figure) typically supported by a plurality of support arms 26 and positioned by piston means 28. Accordingly, the operator will load a blank tube on the front and rear mandrels 24 and cycle the feed section 14 such that one mandrel, e.g. the front mandrel, will drop down and move the blank tube along the longitudinal finning axis 29 into the finning head section 16. When the blank tube is completely enhanced the mandrel will retract to its original position while ejection means, e.g. eject wheels, in the ejection section 32, will engage the enhanced tube and send it into the pore measurement section 18. Once the enhanced tube is completely into the pore measurement section 18 the enhanced tube is matingly engaged by measuring apparatus 40 for measuring the pore size on the surface of the evaporator tube. A fixed reference means 50 provides a reference pressure drop. Once the front mandrel is in its original position, the rear mandrel will drop down and the control system will adjust the finning machine and the enhancing process will repeat itself.

Figure 2:
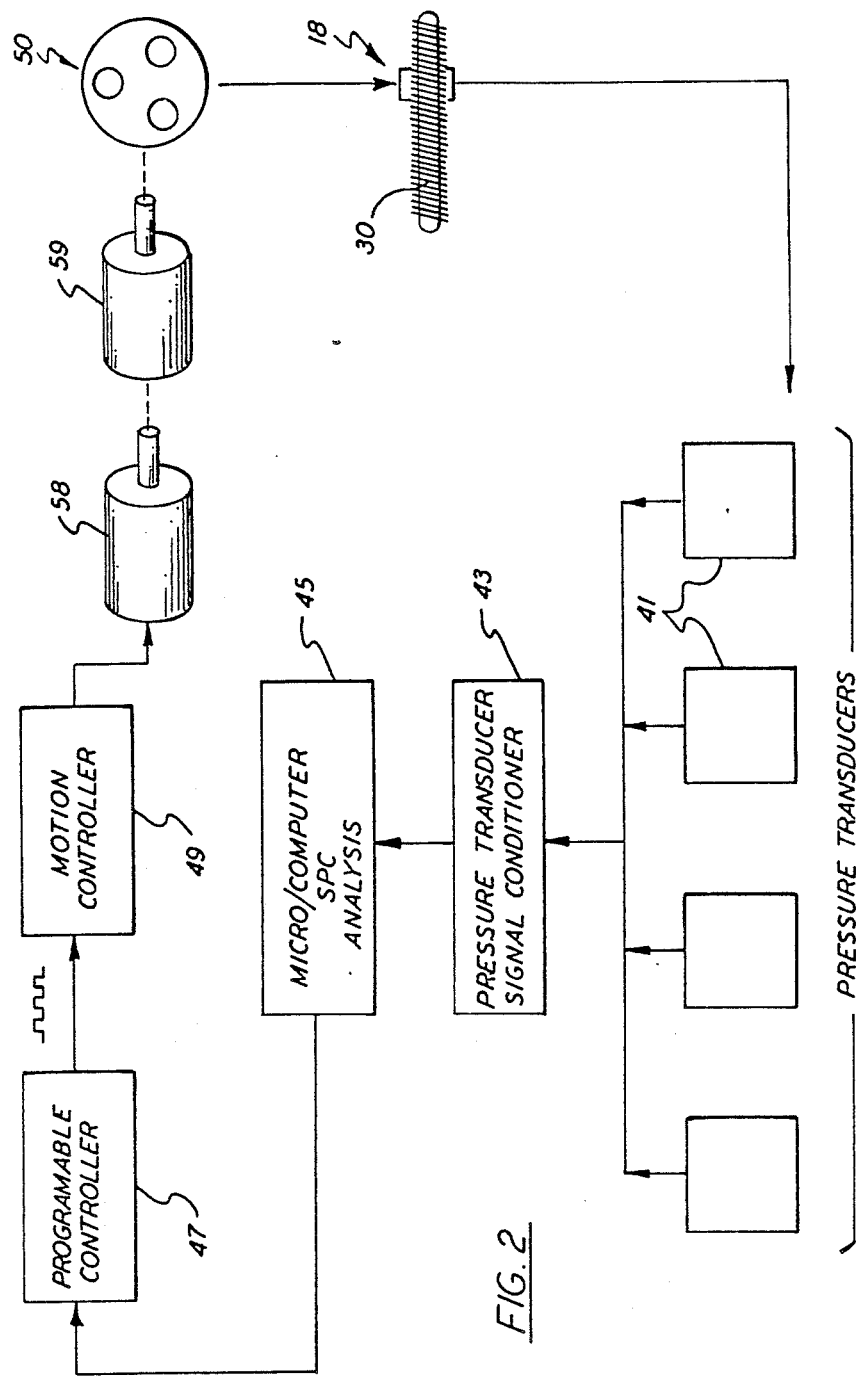
FIG. 2 is a schematic representation of a finning system for an enhanced tube in accordance with the present invention.

FIG. 2 is a schematic illustration of a finning head for the manufacture of enhanced tubes having a closed loop control system for operating the finning head in accordance with the principles of the present invention. The closed loop control system comprises a pore measurement section 18 of a finning station into which a finned tube is ejected after manufacture, and compressed air is blown through the pores of the enhanced tube resulting in a pressure drop across the pores. The resulting pressure drop is sensed by a plurality of pressure transducers 41. The analog output signal from the pressure transducers 41 is fed to a signal conditioner 43 which amplifies and linearizes the output signal and feeds it to microcomputer 45. The computer uses standard statistical process control methods to control manufacturing tolerances that are needed to meet minimum average heat transfer performance of the tubes. The computer monitors changes in the process means for average pore size which may result from process drift or a sudden change in a critical finning variable. If a change in the process is needed, microcomputer 45 provides an electrical analog signal to the programmable controller 47. The programmable controller 47 processes the received electrical signals provided by the microcomputer 45, according to preprogrammed procedures, and generates a digital electrical signal which is then provided to motion controller 49. The motion controller 49 processes the received electrical signal provided by the programmable controller 47 and generates a position signal output. The output of the motion controller 49, a current signal, is fed to servo motor 58 which in turn moves the linear actuator 59 which adjusts the finning head to its new position. After the finning head is adjusted to its new position a new tube is enhanced and the closed loop control system will repeat itself.

Figure 3:
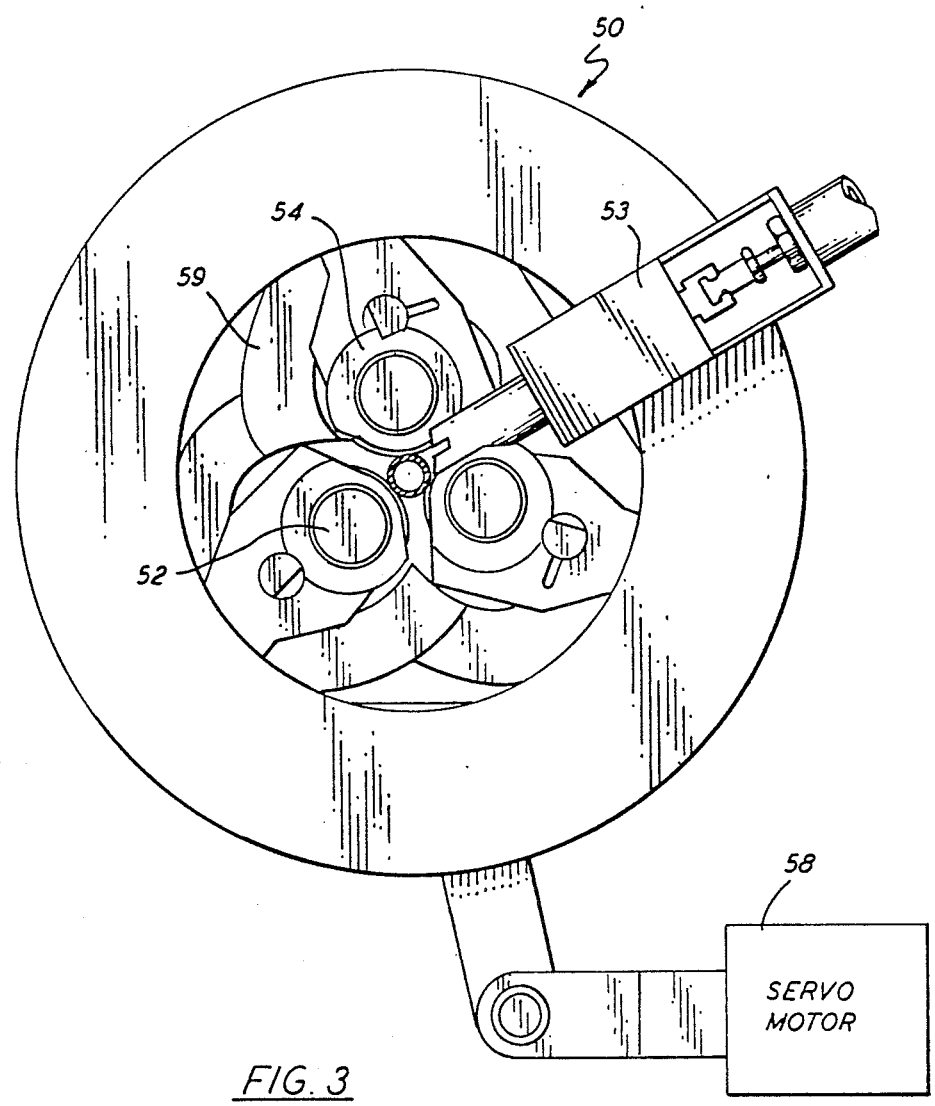
FIG. 3 is a front elevational view of the finning head of the finning machine as shown in FIG. 1.

As shown in FIG. 3, the finning head section includes a finning head 50 having a plurality of tool arbors 52 and a tube locating device 53, which accurately positions the end of the blank tube within finning head 50 prior to the start of the finning process. Each of the tool arbors 52 includes a tool gang arrangement having a plurality of finning discs 54 and rollers, well known in the art, cooperating with the mandrel to produce the enhanced tube. The finning discs 54, which are skewed at an angle to the longitudinal finning axis 29, inherently move the enhanced tube through the finning head section 16 to the ejection section 32. When the blank tube is completely enhanced the finning head 50 of the finning head section 16 will open, i.e. the tool arbors 52 will move radially outward due to the servo motor 58 coacting with camming surface 59, and the mandrel will retract to its original position. Further, as more clearly shown in FIG. 1, after the mandrel is retracted to its original position the ejection means, e.g. eject wheels, in the ejection section 32, will engage the enhanced tube and move it into the cavity measurement section 18 where the closed loop control system will measure the pore size of the enhanced tube and according to procedures will position the tool arbors for optimum tube geometry of the next tube to be manufactured.

Figure 4:
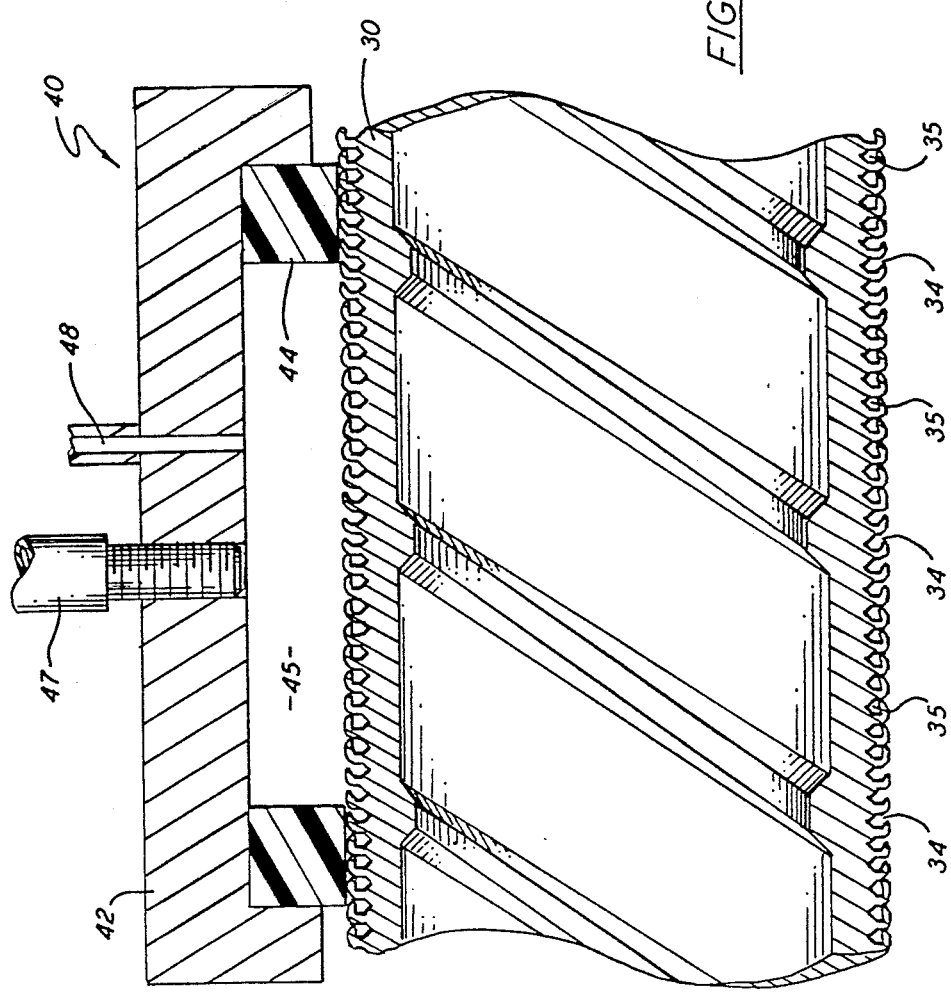
FIG. 4 is a vertical section of a part of an enhanced tube mating with the pore measuring device as shown in FIG. 1.

There is a range in which the microcomputer will control the average pore size in the closed loop manufacturing process. This range is caused by the differences in material properties and dimensions of the blank tubes used. Accordingly, the process uses a distribution of the average pore size for a plurality of tubes in determining the average overall heat transfer performance of the enhanced evaporator tubes in order to meet the minimum average heat transfer performance of the enhanced tube. FIG. 4 shows a typical enhanced evaporator tube 30 consisting of subsurface channels 35 communicating with the surroundings of the tube through the pores 34. The measuring apparatus 40 comprises a rectangular block 42 and a flexible insert 44 having an arcuate longitudinal channel therein whereby the flexible insert matingly engages with the surface of the enhanced tube 30. Flexible insert 44 acts like a gasket against the surface of the enhanced tube. Thus, when air is blown into chamber 45 through inlet 47, and the flexible insert 44 is sealed against the surface of the enhanced tube, the air in chamber 45 enters pores 34 in the surface of the tube within a projected area of the chamber 45 and flows through corresponding subsurface channels 35 and out pores 34 outside the projected area of the chamber to the surroundings. The measuring apparatus 40 thus measures the average pores size on the tube. This average pore size measurement is directly related to the boiling heat transfer coefficient of the tubes.

The present closed loop control system for the manufacture of enhanced evaporator tubes more closely controls the operation of the finning head, as opposed to the prior mechanical adjustments for operator control, and inspects all of the tubes that are produced and automatically adjusts the position of the finning head to maintain the correct pore size. Thus, the closed loop control system requires no operator interaction.

In operation, after each tube is enhanced it is ejected into the pore measurement section 18 where at least one measuring apparatus 40 clamps down on the tube. Compressed dry air is then blown through the pores and the resulting pressure is sensed by the pressure transducer and read by the microcomputer. After a number of tubes have been processed, the microcomputer applies statistical process control procedures to determine whether or not a change in the finning head position is required. If a change in head position is required, the microcomputer sends a signal to the programmable controller indicating the required change. Small changes in the finning head position, accomplished by the servo motor and linear actuator, are sufficient to alter the pore size and bring the process back into proper tolerance limits.

Of course, the foregoing description of a method and control system for manufacturing enhanced tubes is directed to a preferred embodiment, and various modifications and other embodiments of the present invention will be readily apparent to one of ordinary skill in the art to which the present invention pertains. Therefore, while the present invention has been described in conjunction with a particular embodiment, it is to be understood that various modifications and other embodiments of the present invention may be made without departing from the scope of the invention as described herein and as claimed in the appended claims.

What is claimed is:

1. A closed loop control system for a finning head of a production finning machine which has a plurality of tool arbors with a tool gang arrangement for manufacturing an enhanced outer surface of an evaporator tube, having subsurface channels connected to surface pores, comprising:

at least one pneumatic measuring means for measuring the pore size on a portion of the outer surface of the enhanced evaporator tube and generating an electrical signal indicative of the measured pore size;

processor means for receiving said signal indicative of the measured pore size and for processing said signal to determine the different between the measured pore size and a preselected pore size, and for generating an output signal when the determined pore size is different that the preselected pore size; and means for adjusting the tool arbors of the finning head with respect to the outer surface of the next manufactured evaporator tube in response to the generated output signal of said processor means for manufacturing the correct pore size on the surface of the next manufactured evaporator tube.

2. A control system as set forth in claim 1 wherein said preselected pore size is equivalent to an enhanced evaporator tube having an optimum boiling heat transfer coefficient.

* * * * *